(12) United States Patent
Walsh et al.

(10) Patent No.: US 10,214,764 B2
(45) Date of Patent: Feb. 26, 2019

(54) SEPARATION DEVICE FOR USE IN THE SEPARATION, CHARACTERIZATION AND/OR IDENTIFICATION OF MICROORGANISMS

(71) Applicant: bioMerieux, Inc., Durham, NC (US)

(72) Inventors: John Walsh, Durham, NC (US); Jones M. Hyman, Wake Forest, NC (US); Christopher Ronsick, Durham, NC (US); John Link, Durham, NC (US); Ron Robinson, Durham, NC (US); Mark Wilson, Hillsborough, NC (US)

(73) Assignee: BIOMERIEUX, INC., Durham, NC (US)

( * ) Notice: Subject to any disclaimer, the term of this patent is extended or adjusted under 35 U.S.C. 154(b) by 0 days.

(21) Appl. No.: 14/882,099

(22) Filed: Oct. 13, 2015

(65) Prior Publication Data
US 2016/0032348 A1 Feb. 4, 2016

Related U.S. Application Data

(63) Continuation of application No. 12/589,969, filed on Oct. 30, 2009.
(Continued)

(51) Int. Cl.
*B01L 1/00* (2006.01)
*B01L 3/00* (2006.01)
(Continued)

(52) U.S. Cl.
CPC .............. *C12Q 1/24* (2013.01); *B01L 3/5021* (2013.01); *C12Q 1/04* (2013.01); *C12Q 1/37* (2013.01); *C12Q 1/6816* (2013.01); *G01N 21/03* (2013.01); *G01N 21/65* (2013.01); *G01N 33/48735* (2013.01); *G01N 33/6848* (2013.01); *B01L 2300/042* (2013.01);
(Continued)

(58) Field of Classification Search
CPC ....... B01L 3/502753; B01L 2200/0647; B01L 2300/0838; B01L 2400/0409
See application file for complete search history.

(56) References Cited

U.S. PATENT DOCUMENTS

| 4,212,948 A | 7/1980 | Dorn |
| 4,410,630 A | 10/1983 | Zierdt |

(Continued)

OTHER PUBLICATIONS

USPTO; Non-Final Office Action for U.S. Appl. No. 12/589,969 dated May 13, 2015, 11 pages.
(Continued)

*Primary Examiner* — Nathan A Bowers
(74) *Attorney, Agent, or Firm* — Christopher J. Knors; Moore & Van Allen PLLC

(57) ABSTRACT

The present invention is directed to a separation device or container that can be used in the separation, isolation or pelleting of microorganisms from a test samples known to contain or suspected of containing said microorganisms. Subsequently, the separated, isolated or pelleted microorganism sample can undergo one or more interrogation steps to provide measurements useful for the characterization and/or identification of microorganism. In one aspect of the present invention, the interrogation steps can occur in situ in the separation device or container described herein.

10 Claims, 3 Drawing Sheets

Related U.S. Application Data

(60) Provisional application No. 61/110,187, filed on Oct. 31, 2008.

(51) Int. Cl.

| | | |
|---|---|---|
| *C12Q 1/24* | (2006.01) | |
| *C12Q 1/04* | (2006.01) | |
| *G01N 21/65* | (2006.01) | |
| *G01N 33/68* | (2006.01) | |
| *G01N 21/03* | (2006.01) | |
| *C12Q 1/37* | (2006.01) | |
| *C12Q 1/6816* | (2018.01) | |
| *G01N 33/487* | (2006.01) | |
| *G01N 21/35* | (2014.01) | |
| *G01N 21/3581* | (2014.01) | |
| *G01N 21/47* | (2006.01) | |
| *G01N 21/64* | (2006.01) | |
| *G01N 21/359* | (2014.01) | |
| *G01N 33/49* | (2006.01) | |

(52) U.S. Cl.
CPC .......... *B01L 2300/0838* (2013.01); *B01L 2300/0861* (2013.01); *G01N 21/35* (2013.01); *G01N 21/359* (2013.01); *G01N 21/3581* (2013.01); *G01N 21/47* (2013.01); *G01N 21/64* (2013.01); *G01N 33/491* (2013.01)

(56) References Cited

U.S. PATENT DOCUMENTS

| | | |
|---|---|---|
| 5,257,984 A | 11/1993 | Kelley |
| 5,434,139 A | 7/1995 | Ax et al. |
| 5,736,398 A | 4/1998 | Giambernardi et al. |
| 5,840,502 A * | 11/1998 | Van Vlasselaer ..... B01L 3/5021 210/781 |
| 6,121,055 A | 9/2000 | Hargreaves |
| 6,398,719 B1 | 6/2002 | Kaneko et al. |
| 7,070,739 B1 | 7/2006 | Anderson et al. |

OTHER PUBLICATIONS

Ammar, Mohammed Salim, J Fluoresc, "Recent Advances in the Use of Intrinsic Fluorescence for Bacterial Identification and Characterization" vol. 17, Jul. 12, 2007, pp. 455-459.

* cited by examiner

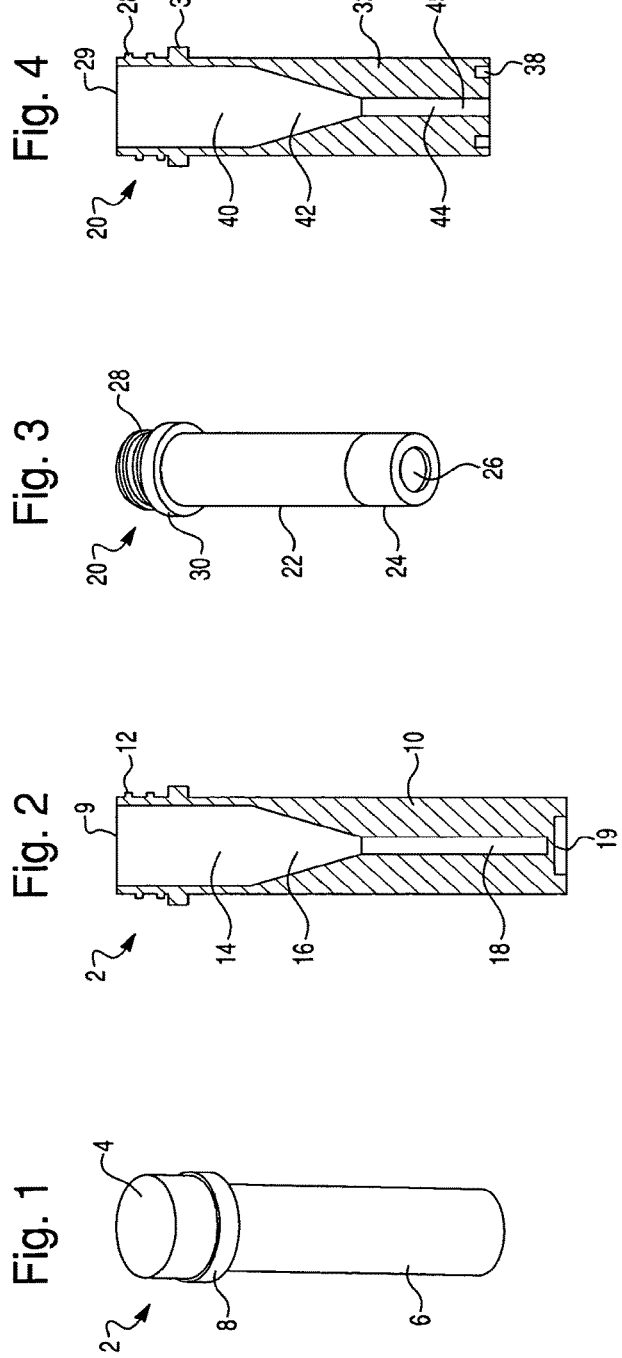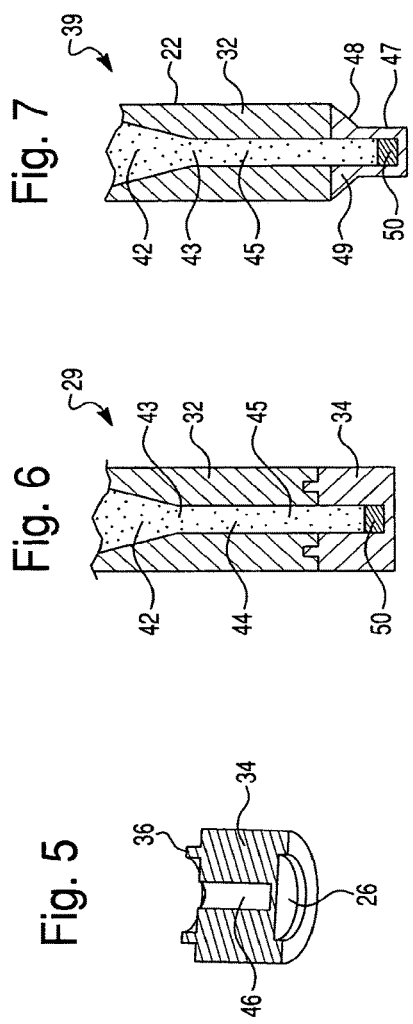

Post-centrifugation of lysed S. aureus-containing blood culture broth

SEPARATION DEVICE FOR USE IN THE SEPARATION, CHARACTERIZATION AND/OR IDENTIFICATION OF MICROORGANISMS

CROSS REFERENCE TO RELATED APPLICATION

This application is a continuation of U.S. patent application Ser. No. 12/589,969, filed Oct. 30, 2009, and claims the benefit of U.S. Provisional Patent Application No. 61/110,187, filed Oct. 31, 2008, which is incorporated herein.

FIELD OF THE INVENTION

The present invention is directed to a separation device for the separation of microorganisms. In particular, the device of the present invention can be used to separate microorganisms for characterization and/or identification.

BACKGROUND OF THE INVENTION

The detection of pathogenic microorganisms in biological fluids should be performed in the shortest possible time, in particular in the case of septicemia for which the mortality remains high in spite of the broad range of antibiotics which are available to doctors. The presence of biologically active agents such as a microorganism in a patient's body fluid, especially blood, is generally determined using blood culture bottles.

Bloodstream infections are associated with high morbidity and mortality, yet current diagnostic methods, of culture followed by biochemical identification and antibiotic susceptibility testing, can take several days to perform. Typically, empiric therapy is initiated based on clinical symptoms, and test results only impact clinical decisions when the initial therapy fails. The ability to characterize bloodstream infections within the first few hours, preferably within an hour, after a positive blood culture result would significantly boost the clinical relevance of the diagnostic information provided. Molecular amplification methods have been proposed to fill this need, but serious challenges to this approach remain. The positive blood culture broth itself represents a naturally amplified population of microorganisms with potential for use in a variety of rapid, identification (ID) tests.

Traditional automated phenotypic ID tests, such as the Vitek®, Phoenix™ and Microscan® systems, or manual phenotypic tests such as API require that microorganisms be in an appropriate growth phase and free of interfering media and blood products in order to provide robust results. These systems use colonies grown from the positive broth for 18-24 hours on plated media. However, in an effort to obtain faster results, some laboratories have reported using these systems with microorganisms isolated from positive blood culture bottles. These direct-from-the-bottle tests are not appropriate for all microorganisms (e.g., Gram-positive cocci), are not validated by the test manufacturers, and generally take 3-8 hours to provide results. Faster and more broadly specific tests are urgently needed in order to provide the physician with clinically relevant results within the first few hours, preferably within an hour, after a positive culture result.

Optical spectroscopy methods, such as intrinsic fluorescence (IF), infrared spectroscopy (FTIR), or Raman spectroscopy, and mass spectrometry methods such as MALDI-TOF, have the potential to allow for identification of microorganisms very quickly, but may encounter interference from the many highly fluorescent and absorptive compounds present in liquid microbiological culture media and in clinical samples such as blood or combinations thereof. The most commonly employed methods for recovering microorganisms directly from positive blood culture broth are two-step differential centrifugation and centrifugation in a serum separator tube. However, these methods have several drawbacks. The resultant microbial preparation often contains contaminating red blood cells, platelets, lipid particles, plasma enzymes and cellular debris, which can cause poor results in traditional phenotypic ID tests. These methods are also very labor-intensive and unsafe due to steps which can result in aerosol exposure of potentially dangerous pathogens to the user. Simple, safe and reliable methods are needed to isolate microorganisms from blood culture broth and other complex samples that are free of these interfering materials and compatible with rapid identification technologies.

SUMMARY OF THE INVENTION

The present invention is directed to a separation device or container that can be used for the separation of microorganisms from a sample that contains or is suspected of containing microorganisms. In accordance with the present invention, the separation device can be used for the separation or pelleting of an unknown microorganism and subsequent interrogation of the separated sample or pellet for characterization and/or identification of the unknown microorganism.

In one aspect, the present invention is directed to a container for isolating and identifying a microorganism, said container comprising:
(a) an upper portion having a wide internal diameter;
(b) a lower portion having a narrow internal diameter; and
(c) an optical window on the bottom, top and/or one or more sides of the container, said optical window being transparent to at least a portion of the near infrared, visible, and/or ultraviolet light spectrum. Optionally, the container may additionally have a middle tapered section connecting the wide internal diameter of the upper portion with the narrow internal diameter of the lower portion.

In another aspect, the present invention is directed to a disposable separation device, comprising:
(a) a cylinder shaped container comprising a body having a longitudinal axis, the body defining an elongate internal capillary tube oriented along the axis having a first end and a second end, the body further defining a reservoir connected to the first end of the capillary tube;
(b) wherein the body proximate to the second end of the capillary tube is made from an optically transparent material;
(c) a cover for the reservoir for enabling access to the reservoir permitting a fluid sample to be dispensed into the reservoir.
Optionally, the cylinder shaped container may contain a density cushion within the reservoir. The container may additionally have a tapered section connecting the reservoir and the capillary tube.

In one embodiment of the present invention, the microbial agent is separated or pelleted at the bottom of the capillary tube located in the separation device or container in the manner described herein. The separated or pelleted microbial agent can be interrogated for characterization and/or identification of the microbial agent.

In another embodiment, the separation device can be sealed, for example, the device can be hermetically sealed. Such devices can provide safety advantages when handling potentially infectious agents. In other possible embodiments, the separation device can provide a means to access the separated, isolated, or pelleted microorganism sample, thereby allowing the sample to be removed from the separation device prior to interrogation, or for additional testing.

BRIEF DESCRIPTION OF THE FIGURES

FIG. 1 is a perspective view of a separation device, in accordance with one embodiment of the present invention.

FIG. 2 is a cross-sectional view of the separation device of FIG. 1.

FIG. 3 is a perspective view of a separation device, in accordance with another embodiment of the present invention.

FIG. 4 is a cross-sectional view of the top portion of the separation device shown in FIG. 3.

FIG. 5 is a cross-sectional view the bottom portion of the separation device shown in FIG. 3. The bottom portion of the separation device is fitted to the lower end of top portion of the separation device of FIG. 4.

FIG. 6 is a cross-sectional view of the separation device of FIG. 3, showing a separated microbial agent in the capillary tube section of the separation device (e.g., the pellet after centrifugation).

FIG. 7 is a cross-sectional view of another embodiment of the bottom portion of the separation device of FIG. 3. As shown, this embodiment has two indented opposing sides leading to adjacent narrow side walls, thus allowing the separated microbial agent in the capillary tube section to be interrogated from the side of the separation device.

DETAILED DESCRIPTION OF THE INVENTION

Figure 11:
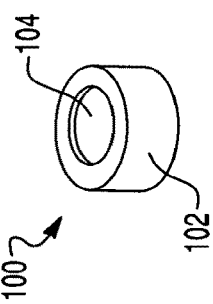
FIG. 11 is a perspective view of an alternative cap for the separation device of the present invention.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Methods for the separation, characterization and/or identification of microorganisms have been disclosed in the following commonly assigned U.S. patent applications: (1) Ser. No. 12/589,929 entitled "Method for the Isolation and Identification of Microorganisms", filed Oct. 30, 2009; (2) Ser. No. 12/589,952 entitled "Method for Separation, Characterization and/or Identification of Microorganisms using Spectroscopy", filed Oct. 30, 2009; (3) Ser. No. 12/589,936 entitled "Method for Separation, Characterization and/or Identification of Microorganisms using Mass Spectrometry", filed Oct. 30, 2009; and (4) Ser. No. 12/589,976 entitled "Method for Separation, Characterization and/or Identification of Microorganisms using Raman Spectroscopy", filed Oct. 30, 2009. These applications are incorporated herein by reference. Briefly, these inventions disclosed methods for isolating, characterizing and/or identifying microorganisms in a sample. The methods allow for the separation, characterization and/or identification of microorganisms more quickly than prior techniques, resulting in faster diagnoses (e.g., in a subject having or suspected of having septicemia) and identification of contaminated materials (e.g., foodstuffs and pharmaceuticals). In these, and other methods of characterizing and/or identifying microorganisms, it is often necessary to provide a separated, isolated, or pelleted microorganism sample for subsequent characterization and/or identification procedures. The present invention discloses a separation device that can be used for the separation, isolation and/or pelleting of microorganisms from a sample. For example, the separation device of the present invention can be used to pellet microorganisms (e.g., by centrifugation) from a liquid culture (e.g., a blood culture). The microorganism pellet can then undergo one or more interrogation steps to provide measurements useful for characterization and/or identification of the microorganism.

In one embodiment, the interrogation step can be carried out while the separated, isolated or pelleted microorganism sample remains in the separation device. For example, a sealed separation device (e.g., hermetically sealed device) can be used for the preparation of a separated, isolated or pelleted microorganism sample, and subsequently, the separated, isolated or pelleted microorganism sample can be subjected to a non-invasive interrogation technique to provide data or measurements capable of characterization and/or identification of the microorganism. In another embodiment, the separated, isolated, or pelleted microorganism sample can be removed from the separation device prior to interrogation. For example, the separated, isolated or pelleted microorganism can be resuspended in an appropriate buffer and removed (e.g., by pipette) from the device or container. In another embodiment, as disclosed herein, the separation device or container may include a lower portion that is capable of being removed, or snapped apart, from the separation device or container (i.e., a removable lower portion). In operation, this lower portion can be snapped off from the separation device or container to provide access to the separated or isolated microorganisms therein.

In general, the separation device or container of the present invention may be any device or container useful for the separation, isolation or pelleting of a microorganism from a test sample containing or suspected of containing microorganisms. For example, the separation device or container may comprise a single-, or multi-piece body and a closure or cap. The body of the device can be molded, blow-molded, or formed using other well known techniques in the art. In general, any known plastic, glass, or transparent material, or the like, can be used for the separation device. The separation device will be formed have an opening at one end providing access to the interior of the device or container for loading and/or unloading test samples. In embodiment, the separation device or container comprises a cylinder shaped body, which is closed at one and open at an opposite one end. Typically, the closure or cap can employ any known mechanism to close or otherwise seal off the interior of the device or container from the outside environment. For example, the closure or cap may be a snap-type lid that is attached to the body of the device or container and that can be snapped over the opening of the device or container to close or seal the interior of the device from the outside environment. Alternatively, the closure can be a threaded cap that can be screwed onto the device or container to close the device/container. As is well known in the art, the cap can have threads on the inner sidewall of the cap that thread or screw onto threads located on an exterior wall of the device or container. In one embodiment, the cap can contain one or more rubber O-ring on the inside surface thereof, as is well known in the art. The use of one or more O-rings provides a seal (e.g., a hermetic seal). In another possible embodiment, as shown in FIG. 11, the closure or cap 100 may have a pierceable septum 104 capable of being pierced, e.g., by a needle or the like, thereby allowing for the deliver of a test sample into the sealed device or container. The use of a pierceable septum 104 can provide a safety advantage for the user or technician when handling potentially infectious agents and enables automation of the identification method. The pierceable septum 104 also ensures the device or container remains sealed (e.g., hermetically sealed), and thus, provides protection from possible contamination for the separation device.

Test samples that may be subjected to separation, isolation, or pelleting in the separation device or container of the present invention include both clinical and non-clinical samples in which microorganism presence and/or growth is, or may be suspected, as well as samples of materials that are routinely or occasionally tested for the presence of microorganisms. For example, the test sample can be the culture broth from a culture of a clinical or non-clinical specimen sample. Typical specimen samples that may be cultured and subsequently subjected to a separation technique for separation, isolation, or pelleting of microorganisms contained therein, may include, blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, other body fluids, and the like.

In one embodiment, as described further herein, the separation device or container may employ the use of a density cushion for the separation, isolation or pelleting of microorganisms from a test sample. As used herein, the term "density cushion" refers to a solution having a homogenous density throughout. Useful density cushions are further described herein. For example, a test sample known to contain, or that may contain microorganisms can be loaded over a density cushion contained within the device or container, and the container of device centrifuged to isolate or pellet the microorganisms. In accordance with this embodiment, the separation device or container will have sufficient volume to hold a density cushion and a sample. In one embodiment, the container fits or can be fitted into a centrifuge rotor. The volume of the container can be from about 0.1 ml to about 25 ml, e.g., from about 1 ml to about 15 ml, e.g., from about 1.5 ml to about 8 ml. If the separation is done on a microscale, the volume of the container can be from about 2 µl to about 100 µl, e.g., from about 5 µl to about 50 µl. In some embodiments, as discussed in more detail herein, the separation device or container can be preloaded with the density cushion. In some embodiments, an intermediate layer (liquid or solid) can be placed on top of the density cushion before the sample is laid or layered on top in order to prevent any mixing of the density cushion and the sample. For example, a thin membrane can be placed over the prepackaged density cushion to prevent mixing of the density cushion with a test sample added at a later time. In yet another embodiment, the separation device or container can be preloaded with a density cushion and subsequently preloaded with a lysis solution. Useful lysis solutions are disclosed in the commonly assigned U.S. patent applications discussed herein. In accordance with this embodiment, a thin membrane can be used to separated the density cushion and lysis solution, thereby preventing mixing.

In one embodiment, the device or container has an upper internal chamber or reservoir having a wide diameter to hold the test sample and the majority of the density cushion, and a lower internal chamber or capillary tube having a narrow diameter for collecting the separated, isolated or pelleted microorganisms. The upper internal chamber or reservoir can have an internal diameter of about 0.32 to about 0.40 inches, e.g., about 0.34 to about 0.38 inches, e.g., about 0.36 inches. For microscale separations, the internal diameters can be even smaller. For example, the internal diameter of the narrow portion can be about 0.001 to about 0.04 inches, e.g., about 0.002 to about 0.01 inches. The lower internal chamber or capillary tube can have an internal diameter of about 0.04 to about 0.12 inches, e.g., about 0.06 to about 0.10 inches, e.g., about 0.08 inches.

In another embodiment, the device or container is a disposable separation device, comprising a tubular container comprising a body having a longitudinal axis, the body defining an elongate internal capillary tube oriented along the axis having a first end and a second end, the body further defining a reservoir connected to the first end of the capillary tube. In one aspect of this embodiment, the body proximate to the second end of the capillary tube is made from an optically transparent material. A removable closure or cover is provided for the reservoir and enables access to the reservoir permitting a fluid sample to be dispensed into the reservoir. Optionally, a density cushion can be prepackaged into the device or container.

The separation device or container may also have a middle tapered portion or chamber connecting the upper internal chamber or reservoir with the lower internal chamber or capillary tube. The inner sidewalls of the middle tapered portion can be tapered, or can decrease in diameter, between the upper internal chamber or reservoir with the lower internal chamber or capillary tube. The inner sidewalls of the tapered portion can have an angle of about 20 to about 70 degrees, e.g., about 30 to about 60 degrees. In one embodiment, the lower narrow portion is less than half of the total height of the container, e.g., less than about 40%, 30%, 20%, or 10% of the total height of the container.

In certain embodiments, the container is designed such that the separated, isolated, or pelleted microorganisms can be readily recovered from the container after separation, either manually or in an automated manner (so that technicians are not exposed to the container contents). For example, the container can comprise a removable portion or a break-away portion which contains the pellet and which can be separated from the rest of the container. In another embodiment, the container comprises means for access to the pellet after separation, such as one or more ports or permeable surfaces for insertion of a syringe or other sampling device or for drawing off the pellet. In one embodiment, the container can be a tube, e.g., a centrifuge tube. In another embodiment, the container can be a chip or a card. In one embodiment, the container is a stand alone container, i.e., a device for separating a single sample.

The container can comprise an optical window through which the interrogation can occur. The optical window may be on the bottom, top, and/or sides of the container. The window can be composed of any material that is transparent to light (e.g., at least a portion of the near infrared (NIR; 700 nm-1400 nm), ultraviolet (UV; 190 nm-400 nm) and/or visible (VIS; 400 nm-700 nm) light spectrum). Examples of suitable materials include, without limitation, acrylic, methacrylate, quartz, fused silica, sapphire, a cyclic olefin copolymer (COC) and/or a cyclo olefin polymer (COP) (e.g., Zeonex® (Zeonex®, San Diego, Calif.)). In one embodiment, the entire container is made of optical window material. In another embodiment, the container may be prepared (e.g., molded) from two or more separate parts, such as an optical UV-VIS-NIR transparent component for the optical window and another material (e.g., a lower-cost standard molding plastic) to make up the rest of the container. In one embodiment, the optical window is thin enough to permit spectroscopic interrogation, which will depend on the material of the window. In another embodiment, the optical window is as thin as possible to reduce interference with spectroscopic interrogation. For example, the window can have a thickness of less than about 0.20 inches, e.g., less than about 0.15, 0.10, or 0.05 inches.

Referring now to the Figures, several possible configurations for the separation device or container of the present invention will be further illustrated. One possible embodiment of the separation device is shown in FIGS. 1-2. As shown in FIGS. 1 and 2, the separation device 2 comprises a lower portion 6, generally having a cylinder shape, and an upper portion defined by an externally projecting ridge structure or ledge 8, an opening 9, and a closure cap 4. The lower portion 6 comprises a container body 10 that encloses an internal chamber comprising an upper reservoir 14, a middle tapered section 16 and a lower capillary tube 18, all arranged around the longitudinal axis of the container. As shown, the middle tapered section 16 connects the wider diameter upper reservoir 14 and the smaller diameter capillary tube 18. In general, the container body 10 can be molded or otherwise formed from any known plastic material known in the art. The externally projecting ridge structure or ledge 8 can function as a stop for the closure cap 4 and/or can provide a feature allowing for improved gripping of the device by a user. The upper portion of the device may also provide threads 12 on the external wall of the device 2 for threading or screwing the closure cap 4 onto the device 2, thereby closing or sealing the internal chamber. The device may further contain a thin optical window 19 through which the interrogation can occur. In one embodiment, the diameter of the optical window 19 can be designed to match a fiber optic cable and facilitate precise coupling of the device to a spectrometer. As previously described, the optical window 19 comprises a section of the device that is composed of a material that is transparent to light, and through which interrogation can occur. In other embodiments, the entire device may be made from a material that is transparent to light, thereby allowing interrogation therethrough.

In some embodiments, the separation device 2 of this embodiment can be pre-loaded with a density cushion 43 (shown e.g., in FIGS. 6-7) to facilitate the separation, isolation or pelleting of microorganisms. In another embodiment, the density cushion can be added to the separation device 2 just prior to the loading of the sample to be subjected to the separation step described herein. In yet another embodiment, the separation device 2 can be pre-loaded with a density cushion 43 and a lysis solution (not shown) to facilitate sample lysis and separation, isolation or pelleting of microorganisms, as described in the commonly assigned U.S. patent applications referenced herein.

In another embodiment, as shown in FIGS. 3-6 and 8, the separation device 20 can be made of two separate sections, an upper section 22 and a lower section 24, that can be snapped together, or otherwise attached, to form a single separation device 20. The lower section 24 can be removably attached, or permanently attached, to the upper section 22, in general, by any known means in the art. The upper section 22 comprises an upper body 32, generally comprising a cylinder shape, an externally projecting ridge structure or ledge 30, and opening 29. The opening can be closed or sealed using a closure or cap 52 (see FIG. 8). The upper body 32 further defines the upper portions of an internal chamber. The internal chamber comprises an upper reservoir 40, a middle tapered section 42 and the upper part 44 of a capillary tube 45, all arranged around the longitudinal axis of the container. The lower body 34 comprises the lower part 46 of the capillary tube 45. When the upper body 32 and lower body 34 are snapped together, or otherwise affixed, they enclose the upper chamber, again comprising an upper reservoir 40, a middle tapered section 42 and a capillary tube 45. As shown, the middle tapered section 42 connects the wider diameter upper reservoir 40 and the smaller diameter capillary tube 45. The lower body 34 further comprises a structure, for example, a protruding ridge 36 formed in on the top of lower body 34, that can be fitted (e.g., snapped or attached) into a corresponding recess 38 in the bottom of the upper body 32. The lower body 34 of the device 20 may further contain a thin optical window 26 through which the interrogation can occur. As previously described, the optical window 26 comprises a section of the device that is composed of a material that is transparent to light, and through which interrogation can occur. In other embodiments, the entire device may be made from a material that is transparent to light, thereby allowing interrogation therethrough. As previously described, the container is designed such that the separated, isolated, or pelleted microorganisms can be readily recovered from the container after separation, either manually or in an automated manner (so that technicians are not exposed to the container contents). For example, the lower section 24 may be removable after a separation step, thereby allowing a user to access the separated or pelleted microorganisms, which will be contained in the lower part 46 of the capillary tube 45, of the lower section 24.

In some embodiments, the separation device 20 of this embodiment can be pre-loaded with a density cushion 43 (shown e.g., in FIGS. 6-7) to facilitate the separation, isolation or pelleting of microorganisms. In another embodiment, the density cushion can be added to the separation device 20 just prior to the loading of the sample to be subjected to the separation step described herein. In yet another embodiment, the separation device 20 can be pre-loaded with a density cushion 43 and a lysis solution (not shown) to facilitate sample lysis and separation, isolation or pelleting of microorganisms.

Another embodiment of the lower section of the separation device is shown in FIG. 7. The lower section 48 can be removably attached, or permanently attached, to the upper section 22 to form a separation device 39, in accordance with this invention. The upper section 22 and lower section 47 comprises an upper body 32 and a lower body 49, respectively, that define an internal chamber. The internal chamber comprises an upper reservoir (not shown), a middle tapered section 42 and a capillary tube 45. As shown, the lower body 34 further comprises exterior walls that slope inward 48, that result in thin sidewalls on opposite sides of the bottom of the internal capillary tube 45. These thin sidewalls, allow for interrogation of a separated, isolated or pellet microorganism 50 through the side of the separation device.

Figure 10:
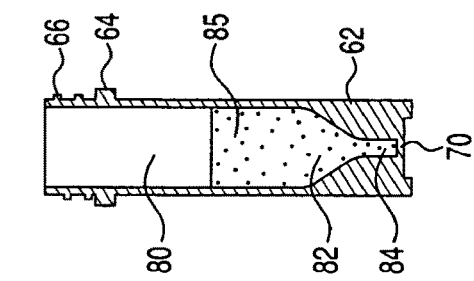
FIG. 10 is a cross-sectional view of the separation device of FIG. 9.
Figure 9:
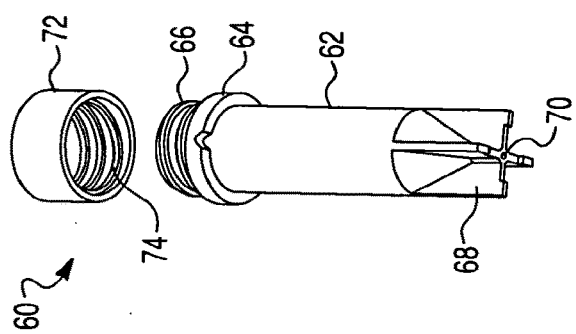
FIG. 9 is a perspective view of yet alternative embodiment of the separation device of the present invention.

In yet another embodiment of the separation device 60 is shown in FIGS. 9-10. Referring to these Figures, the separation device 60 consists of a body 62 that defines an upper reservoir 80, a middle tapered section 82 and a lower capillary tube 84. The middle tapered section 82 connects the larger diameter upper reservoir 80 with the lower capillary tube 84. The upper reservoir 80 is accessed via a removable closure or cap 72 that can be threaded or screwed onto threads 66 formed at the top exterior wall of the body 62. In accordance with this embodiment, the lower portion of the body 62 comprises four stabilizing wings 68 used to provide stability to the separation device 60 when standing upright, e.g., on a table. In another embodiment, the four indents on the bottom of the wings 68 create a recessed area for the precise coupling of a fiber optic probe. Centering of the excitation beam in such a way resulted in improved fluorescence reproducibility and reduced contamination of the emission signal by stray scattered light. The separation device 60 further comprises an optical window 70 formed in the body 62 at the bottom of the capillary tube 84. The optical window 70 comprises a small section of reduced thickness on the body 62, through which the separated, isolated, or pelleted microorganism can be interrogated. As described herein, the optical window 70 can be made from an optically transparent material.

In some embodiments, the separation device 60 of this embodiment can be pre-loaded with a density cushion 85 (as shown e.g., in FIG. 10) to facilitate the separation, isolation or pelleting of microorganisms. In another embodiment, the density cushion can be added to the separation device 60 just prior to the loading of the sample to be subjected to the separation step described herein. In yet another embodiment, the separation device 60 can be preloaded with a density cushion and a lysis solution to facilitate sample lysis and separation, isolation or pelleting of microorganisms.

Figure 8:
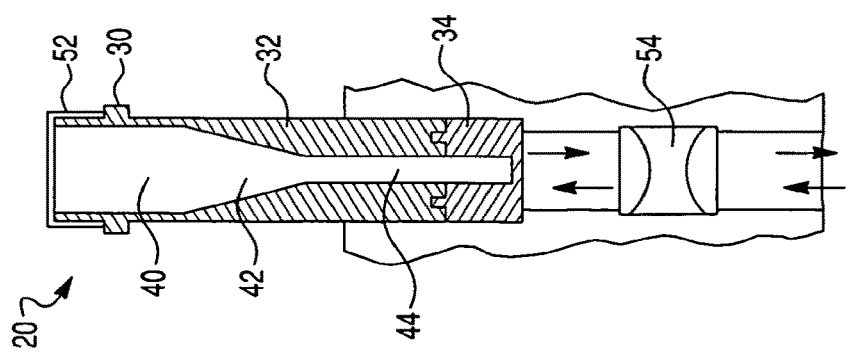
FIG. 8 is a schematic illustration of the concentrated microbial agent in the separation device of FIG. 6 being interrogated through the bottom of the tube by an interrogation module.

FIG. 8 shows the operation of interrogation of concentrated microbial agent 50 within the separation device 60. In one embodiment, the separated, isolated or pelleted microorganisms can be interrogated using any known means in the art (represented here as an interrogation means 58). For examples, as disclosed in co-pending U.S. patent application Ser. No. 12/589,929, titled "Method for the Isolation and Identification of Microorganisms", filed Oct. 30, 2009, the interrogation step can be carried out using intrinsic fluorescence spectroscopy, Raman spectroscopy or other optical technique.

While in the above embodiment the concentrated microbial agent is interrogated while it is still located within the separation device, it is also contemplated that the separated, isolated or pelleted microorganism sample can be removed from the separation device and interrogated, for example, using Mass Spectrometry, as disclosed in co-pending U.S. patent application Ser. No. 12/589,936, titled "Method for Separation, Characterization and/or Identification of Microorganisms using Mass Spectrometry", filed Oct. 30, 2009.

As noted hereinabove, the separation, isolation or pelleting step can be carried out to separate the microorganisms from other components of the sample (e.g., non-microorganisms or components thereof) and to concentrate the microorganisms into a separated, isolated or pellet sample that can be interrogated for identification and characterization purposes. The separation or pelleting step does not have to be complete, i.e., it is not required that 100% separation occur. All that is required is that the separation of the microorganisms from other components of the sample be sufficient to permit interrogation of the microorganisms without substantial interference from the other components. For example, the separation can result in a microorganism pellet that is at least about 10, 20, 30, 40, 50, 60, 70, 80, 90, 95, 96, 97, 98, or 99% pure or higher.

In one embodiment, as described more fully in the commonly assigned U.S. patent applications discussed herein, the separation is carried out by a centrifugation step in which a test sample (e.g., a lysed sample) is placed on top of a density cushion in a separation container and the container centrifuged under conditions which allow the microorganisms to be isolated (e.g., the microorganisms can form a pellet at the bottom and/or sides of the container). In accordance with this embodiment, other components of the sample (e.g., non-microorganisms or components thereof that may be present in the sample medium) stay on top of the density cushion or within the top portion of the density cushion. This separation step isolates the microorganisms away from materials in the sample, such as medium, cell debris, and/or other components that might interfere with interrogation of the microorganisms (e.g., by intrinsic fluorescence). In one embodiment, the density cushion also serves to separate live microorganisms from dead microorganisms (which do not pass through the density cushion). In another embodiment the density cushion does not comprise a density gradient, either before or after the centrifugation. In other words, the separation container is not centrifuged for a sufficient amount of time and/or acceleration for the material making up the density cushion to form a density gradient.

The density of the cushion is selected such that the microorganisms in the sample pass through the cushion while other components of the sample (e.g., blood culture broth, cell debris) remain on top of the cushion or do not pass all of the way through the density cushion. The density cushion may also be selected to separate live microorganisms (which pass through the cushion) from dead microorganisms (which do not pass through the cushion). Suitable densities will depend on the material used in the density cushion and on the sample to be separated. In one embodiment, the density of the cushion is in the range of about 1.025 to about 1.120 g/ml, e.g., about 1.030 to about 1.070 g/ml, about 1.040 to about 1.060 g/ml or any range between about 1.025 to about 1.120 g/ml. In another embodiment, the density of the cushion is about 1.025, 1.030, 1.035, 1.040, 1.045, 1.050, 1.055, 1.060, 1.065, 1.070, 1.075, 1.080, 1.085, 1.090, 1.095, 1.100, 1.105, 1.110, 1.115, or 1.120 g/ml.

The material for the density cushion can be any material that has the appropriate density range for the methods of this invention. In one embodiment, the material is colloidal silica. The colloidal silica may be uncoated (e.g., Ludox® (W.R. Grace, CT)) or coated, e.g., with silane (e.g., PureSperm® (Nidacon Int'l, Sweden) or Isolate® (Irvine Scientific, Santa Ana, Calif.)) or polyvinylpyrrolidone (e.g., Percoll™, Percoll™ Plus (Sigma-Aldrich, St. Louis, Mo.)). In one embodiment, the colloidal silica exhibiting the least interference with spectroscopic interrogation is selected, e.g., the material with the lowest intrinsic fluorescence. The colloidal silica may be diluted in any suitable medium to form the proper density, e.g., balanced salt solutions, physiological saline, and/or 0.25 M sucrose. Suitable densities can be obtained with colloidal silica at a concentration of about 15% to about 80% v/v, e.g., about 20% to about 65% v/v. Another suitable material for density cushions is an iodinated contrast agent, e.g., iohexol (Omnipaque™ NycoPrep™, or Nycodenz®) and iodixanol (Visipaque™ or OptiPrep™). Suitable densities can be obtained with iohexol or iodixanol at a concentration of about 10% to about 25% w/v, e.g., about 14% to about 18% w/v, for blood culture samples. Sucrose can be used as a density cushion at a concentration of about 10% to about 30% w/v e.g., about 15% to about 20% w/v, for blood culture samples. Other suitable materials that can be used to prepare the density cushion include low viscosity, high density oils, such as microscope immersion oil (e.g., Type DF; Cargille Labs, New York), mineral oil (e.g., Drakeol® 5, Draketex 50, Peneteck®; Penreco Co., Pennsylvania), silicone oil (polydimethylsiloxane), fluorosilicone oil, silicone gel, metrizoate-Ficoll® (LymphoPrep™), e.g., at a concentration of about 75% to about 100% for blood culture samples, diatrizoate-dextran (PolymorphoPrep™), e.g., at a concentration of about 25% to about 50% for blood culture samples, carboxymethyl cellulose, hydroxypropylmethyl cellulose, polyethylene oxide (high molecular weight), Pluronic® F127, Pluronic® F68, mixtures of Pluronic® compounds, polyacrylic acid, cross-linked polyvinyl alcohol, cross-linked polyvinyl pyrrolidine, PEG methyl ether methacrylate, pectin, agarose, xanthan, gellan, Phytagel®, sorbitol, Ficoll® (e.g., Ficoll® 400 at a concentration of about 10% to about 15% for blood culture samples), glycerol, dextran (e.g., at a concentration of about 10% to about 15% for blood culture samples), glycogen, cesium chloride (e.g., at a concentration of about 15% to about 25% for blood culture samples), perfluorocarbon fluids (e.g., perfluoro-n-octane), hydrofluorocarbon fluids (e.g., Vertrel XF), and the like as are well known in the art. In one embodiment, the density cushion is selected from one or more of colloidal silica, iodixanol, iohexol, cesium chloride, metrizoate-Ficoll®, diatrizoate-dextran, sucrose, Ficoll® 400, and/or dextran in any combination. The density cushion can also be made up of a combination of materials, e.g., a combination of colloidal silica and oil. Certain combinations of the above compounds may be beneficial for the separation and reading steps of the present invention. For example, combinations of compounds with different UV-quenching properties, such as cesium chloride and Iohexol.

The volume/height of the density cushion should be sufficient to achieve separation of the microorganisms from other sample components. The volume will depend on the size and shape of the separation container. In general, a volume of about 0.1 to about 5 ml can be used, e.g., about 0.2 to about 1 ml, e.g., about 0.2 ml to about 0.5 ml. If the separation is performed on a microscale, the volume of the density cushion can be about 1 µl to about 100 µl, e.g., about 5 µl to about 50 µl. The volume of sample laid or layered on top of the density cushion should be sufficient to provide enough microorganisms to produce a pellet suitable for interrogation. In general, any volume that fits into the container can be used. For example, a volume of about 0.1 ml to about 5 ml can be used, e.g., about 0.2 ml to about 1 ml, e.g., about 0.2 ml to about 0.5 ml. If the separation is performed on a microscale, the volume of sample can be about 1 µl to about 100 µl, e.g., about 5 µl to about 50 µl. The available space in the container for sample will depend on the size and shape of the container. In some embodiments, an intermediate layer (liquid or solid) can be placed on top of the density cushion before the sample is laid or layered on top in order to prevent any mixing of the density cushion and the sample. In one embodiment, the intermediate layer can be polyethylene beads. In another embodiment, a small air bubble can be positioned between the density cushion and the sample to prevent mixing. In a further embodiment, the density cushion can be layered on top of a high density material (e.g., a perfluorocarbon fluid) such that the microorganisms pass through the density cushion during the separation and collect at the interface between the density cushion and the high density material.

In one embodiment of the invention, the separation container is centrifuged in a swing out rotor so that the microorganisms form a pellet directly on the bottom of the container. The container is centrifuged at a sufficient acceleration and for a sufficient time for the microorganisms to be separated (e.g., a pellet formed) from other components of the sample. The centrifugation acceleration can be about 1,000×g to about 20,000×g, e.g., about 2,500×g to about 15,000×g, e.g., about 7,500×g to about 12,500×g, etc. The centrifugation time can be about 30 seconds to about 30 minutes, e.g., about 1 minute to about 15 minutes, e.g., about 1 minute to about 5 minutes. The centrifugation can be carried out at a temperature of about 2° C. to about 45° C., e.g., about 15° C. to about 40° C., e.g., about 20° C. to about 30° C. In one embodiment, the separation container comprises a closure, and the closure is applied to the container to form a hermetic seal prior to centrifugation. The presence of a closure decreases the risks from handling microorganisms that are or may be infectious and/or hazardous, as well as the risk of contaminating the sample. One of the advantages of the methods of the invention is the ability to carry out any one or more of the steps of the methods (e.g., lysis, separation, interrogation, and/or identification) with the microorganisms in a sealed container (e.g., a hermetically sealed container). The present methods, involving the use of automated systems, avoid the health and safety risks associated with handling of highly virulent microorganisms, such as occurs with recovery of microorganisms from samples for direct testing. In one embodiment, the container is not centrifuged for a sufficient time and/or force for a density gradient to form within the density cushion. The present invention does not involve ultracentrifugation of samples, e.g., centrifugation at forces greater than about 100,000×g. Further, the present invention does not involve isopycnic (equilibrium) sedimentation or banding.

Once the separated, isolated or pelleted microorganism sample has been prepared, a subsequent interrogation step can be carried out to provide measurements useful for characterization and/or identification of the microorganism. Useful interrogation means are known in the art. Additional interrogation means are described in the commonly assigned U.S. patent applications discussed hereinabove.

EXAMPLES

Example 1. Devices and Methods for the In Situ Identification of Purified Microbial Pellet To explore the potential of the rapid in situ separation and identification of microorganisms in a separation device, several devices were designed and molded from UV-transparent plastic, in accordance with this invention. These devices contained several common features, including a closure, sample reservoir and a tapered optical quality lower region to enable spectroscopic interrogation of the sedimented microbial pellet from below and/or the side, and features that facilitated the coupling of the device to a spectrofluorimeter. The devices must also be capable of withstanding relatively high g-forces during the separation step. Several iterations of this tube were designed to improve microbial recovery, fluorescence reproducibility and reduce contamination by stray scattered light. The tube was also designed to be hermetically sealed.

Optical interrogation of the sedimented microbial pellet was achieved by either inserting the separation device into a custom-built adapter placed within the sample compartment of the spectrofluorimeter or by coupling the separation device directly to a bifurcated six-around-one 300-400 micron fiber optic cable (Ocean Optics, Dunedin, Fla.) attached to the spectrofluorimeter (Fluorolog® 3 from HORIBA Jobin Yvon Inc., New Jersey). A three-mirror fiber optic adapter was built to enable the use of both the systems detectors (PMT and CCD). Full Excitation-Emission Matrix (EEM) spectra were collected on each microbial pellet (scan range: Excitation 260-800 nm; Emission 260-1100 nm; increments of 5 nm).

Gage reproducibility and reliability studies were performed on the disposable device-fiber optic cable configuration using purified tryptophan and riboflavin solutions. Target CV's of <2.5% were obtained for both fluorophores, confirming the quality of the disposable and the research platform.

Figure 12:
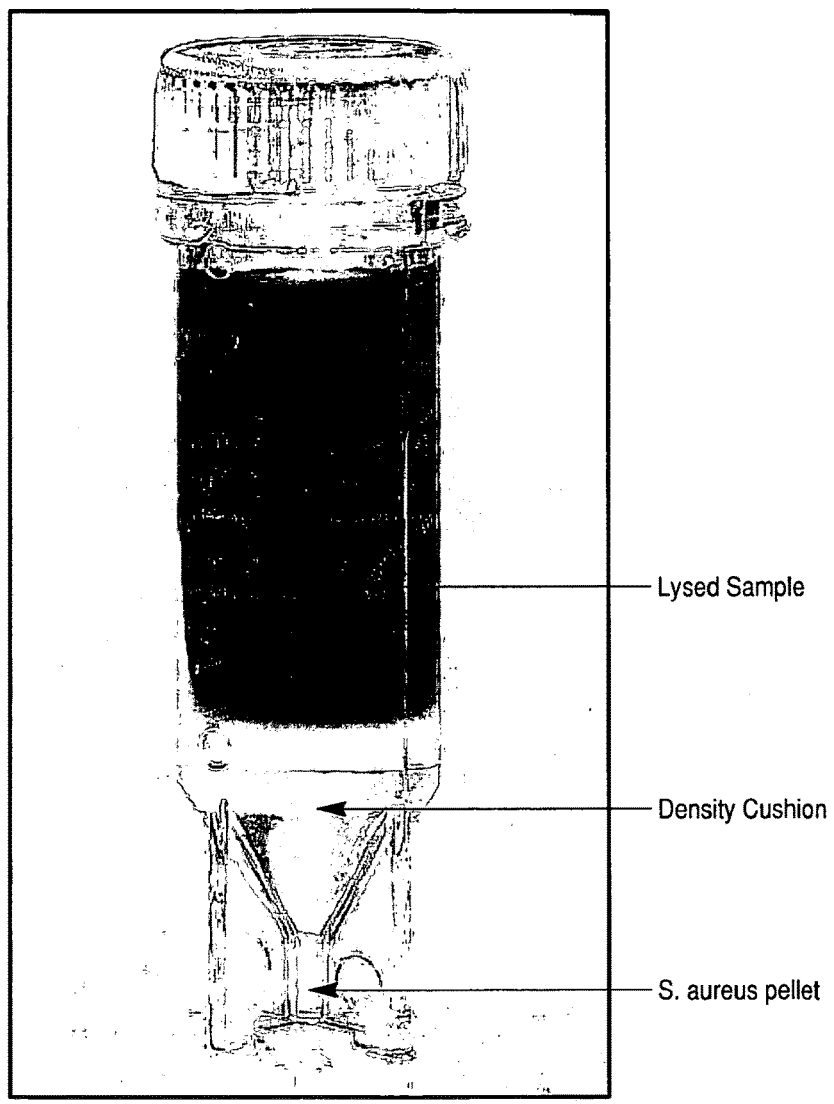
FIG. 12 shows a photograph of a separation device in accordance with one embodiment of the present invention. Clearly visible in the photograph are the lysed sample, density cushion and a microorganism pellet, in accordance with the present invention.

These devices proved useful for the separation and interrogation of microorganisms from a culture medium. FIG. 12 shows an example device after separation by centrifugation of a lysed blood culture sample containing *S. aureus* using a density cushion. Clearly visible in the photograph are the lysed sample, density cushion and a microorganism pellet, in accordance with the present invention.

The invention claimed is:

1. A method comprising the steps of:
    separating at least a portion of a liquid sample in a container, the container comprising:
        a longitudinal axis;
        an upper portion having an opening;
        a lower portion extending from the opening, the lower portion having a generally cylindrical outer shape, the lower portion comprising
            an internal chamber, the internal chamber comprising an upper reservoir, and a middle tapered section connecting the upper reservoir to a capillary tube of diameter smaller than that of the upper reservoir, the upper reservoir, the middle tapered section and the lower capillary tube arranged around the longitudinal axis of the container;
        an optical window transparent to light and configured for interrogation of a portion of the capillary tube; and
        a closure cap operably positioned about the opening;
    pelletizing at least a portion of the liquid sample from the separating step so as to form an isolated, pelletized microorganism or contaminant sample;
    interrogating at least a portion of the isolated, pelletized microorganism or contaminant sample from the pelletizing step; and
    characterizing and/or identifying one or more of microorganisms or contaminants present in the isolated, pelletized microorganism or contaminant sample
    wherein the separating step does not result in banding.

2. The method of claim 1, wherein the liquid sample is a blood culture.

3. The method of claim 1, wherein the container comprises a density cushion and the separating step comprises centrifuging the container for a sufficient time and/or force that substantially prevents a density gradient from forming within the density cushion.

4. The method of claim 1, wherein the separating step does not result in isopycnic sedimentation.

5. The method of claim 1, wherein the separating step and/or the pelletizing step is not complete prior to carrying out the interrogating step.

6. The method of claim 1, wherein the container further comprises a lysing solution and the separating step comprises lysing the sample.

7. The method of claim 1, wherein the interrogation step is carried out while the separated, isolated or pelleted microorganism sample is present in the container.

8. The method of claim 1, wherein the interrogating step comprises a non-invasive interrogation technique.

9. The method of claim 1, wherein the interrogating step is intrinsic fluorescence spectroscopy, Raman spectroscopy, or Mass Spectrometry.

10. A method comprising the steps of:
    separating, without banding and isopycnic sedimentation, at least a portion of a liquid sample in a container, the container comprising:
        a longitudinal axis;
        an upper portion having an opening;
        a lower portion extending from the opening, the lower portion having a generally cylindrical outer shape, the lower portion comprising
            an internal chamber, the internal chamber comprising an upper reservoir, and a middle tapered section connecting the upper reservoir to a capillary tube of diameter smaller than that of the upper reservoir, the upper reservoir, the middle tapered section and the lower capillary tube arranged around the longitudinal axis of the container;
        an optical window transparent to light and configured for the interrogation of a portion of the capillary tube;
        a closure cap operably positioned about the opening; wherein the container comprises a density cushion; and
    centrifuging the container for a sufficient time and/or force that substantially prevents a density gradient from forming within the density cushion;
    pelletizing at least a portion of the liquid sample from the centrifuging step so as to form an isolated, pelletized microorganism or contaminant sample;
    interrogating at least a portion of the isolated, pelletized microorganism or contaminant sample from the pelletizing step; and
    characterizing and/or identifying one or more of microorganisms or contaminants present in the isolated, pelletized microorganism or contaminant sample.

* * * * *

UNITED STATES PATENT AND TRADEMARK OFFICE
CERTIFICATE OF CORRECTION

PATENT NO. : 10,214,764 B2  
APPLICATION NO. : 14/882099  
DATED : February 26, 2019  
INVENTOR(S) : John Walsh et al.

Page 1 of 1

It is certified that error appears in the above-identified patent and that said Letters Patent is hereby corrected as shown below:

On the Title Page

Item (72) Inventors:  
Please change the information for the first inventor to:  
John Walsh, Bahama, NC (US)

Signed and Sealed this  
Thirtieth Day of April, 2019

Andrei Iancu  
*Director of the United States Patent and Trademark Office*